US010571532B2

(12) United States Patent
Zheng et al.

(10) Patent No.: US 10,571,532 B2
(45) Date of Patent: Feb. 25, 2020

(54) CESIUM OPTICAL PUMP DETECTOR FOR BURIED AND ABANDONED CHEMICAL WEAPONS (71) Applicant: Tsinghua University, Beijing (CN)

(72) Inventors: Xiao-Ping Zheng, Beijing (CN); Hua Geng, Beijing (CN)

(73) Assignee: TSINGHUA UNIVERSITY, Beijing (CN)

(*) Notice: Subject to any disclaimer, the term of this patent is extended or adjusted under 35 U.S.C. 154(b) by 0 days.

(21) Appl. No.: 16/233,135

(22) Filed: Dec. 27, 2018

(65) Prior Publication Data

US 2019/0377038 A1 Dec. 12, 2019

Related U.S. Application Data (63) Continuation of application No. PCT/CN2018/075037, filed on Feb. 2, 2018.

(30) Foreign Application Priority Data

Dec. 29, 2017 (CN) .......................... 2017 1 1486875

(51) Int. Cl.
G01R 33/26 (2006.01)
G01R 33/032 (2006.01)
G01V 3/08 (2006.01)

(52) U.S. Cl.
CPC ........... *G01R 33/26* (2013.01); *G01R 33/032* (2013.01); *G01V 3/08* (2013.01)

(58) Field of Classification Search
CPC ......... G01R 33/26; G01R 33/032; G01V 3/08
See application file for complete search history.

(56) References Cited

U.S. PATENT DOCUMENTS

2009/0001979 A1 1/2009 Kawabata
2016/0146909 A1* 5/2016 Kawabata ............... G01R 33/26
324/304
2017/0023654 A1* 1/2017 Kobayashi ............. G01R 33/26

FOREIGN PATENT DOCUMENTS

CN 103852737 A 6/2014
CN 104181604 A 12/2014
(Continued)

OTHER PUBLICATIONS

Data Acquisition system of Cesium OpticaJulyl-Pump Magnetometer Based on STM32, Peng Jun-Jie et,al, Instriment Technique and Sensor, Jul. 2016, No. 7, pp. 75-78.
(Continued)

*Primary Examiner* — Amy He (57) ABSTRACT

A cesium optical pump detector for buried and abandoned chemical weapons of Japan is provided, comprising a pumping light generation module, a first optical module, a magnetic resonance module, a photoelectric detection module, and a signal processing module. The signal processing module includes an amplifying and filtering unit, a self-oscillation unit, a measuring unit, and a calculating unit connected in sequence. The amplifying and filtering unit comprises a first band-pass filter configured to coarsely measure a frequency of the electrical signal and a second band-pass filter configured to finely measure the frequency of the electrical signal. The self-oscillation unit comprises a first phase shifter connected to the first band-pass filter and a second phase shifter connected to the second band-pass filter. In the present disclosure, the intensity of a magnetic field detected can be finely measured, so that the ACWs can be found efficiently and accurately.

18 Claims, 3 Drawing Sheets (56) References Cited

FOREIGN PATENT DOCUMENTS

| | | |
|---|---|---|
| CN | 204719241 U | 10/2015 |
| CN | 106802397 A | 6/2017 |
| CN | 206400119 U | 8/2017 |

OTHER PUBLICATIONS

Field-weakening Detecting System Based on Larmor Frequency Measurement, Hu Qing et.al, Instriment Technique and Sensor, Oct. 2017, No. 10, pp. 67-69.
Design on Cesium Optical Pumping Weak Magnetic Detection System, Chen Yongtai et. al, Journal of WUT Information &Management Engineering), Oct. 2014, vol. 36, No. 5, pp. 600-603.
International Search Report of PCT/CN2018/075037.
Development and Application of Optical Pump Atomic Magnetometer based on MEMS Technology, Zhang Peng et. al, Micronanoelectronic Technology, vol. 54, No. 7, Jul. 2017, pp. 465-471.

\* cited by examiner

CESIUM OPTICAL PUMP DETECTOR FOR BURIED AND ABANDONED CHEMICAL WEAPONS

CROSS-REFERENCE TO RELATED APPLICATIONS

This application claims all benefits accruing under 35 U.S.C. § 119 from China Patent Application No. 201711486875.7, filed on Dec. 29, 2017 in the State Intellectual Property Office of China, the content of which is hereby incorporated by reference. This application is a continuation under 35 U.S.C. § 120 of international patent application PCT/CN2018/075037 filed on Feb. 2, 2018, the content of which is also hereby incorporated by reference.

FIELD

The present disclosure relates to the field of detection, in particular to a cesium optical pump detector for buried and abandoned chemical weapons.

BACKGROUND

Since the end of the Second World War, huge amount of Abandoned Chemical Weapons (hereinafter to be referred as ACWs) still present in many countries pose a grave threat to people's lives and health, as well as environmental security. Now over 70 years have passed, the ACWs have been corroded seriously, which may have caused or will cause leakage of the highly toxic chemicals. Except for the high toxicity, wide distribution is another characteristic of the ACWs. So it would be of great significance to develop detector to find the ACWs.

As mentioned above, the ACWs are continuously corroding, and materials of packaging housings of the ACWs have been transformed to rust from metal such as iron or steel. Therefore, conventional detectors are not appropriate for the ACWs.

SUMMARY

According to an aspect of the present disclosure, a cesium optical pump detector for buried and abandoned chemical weapons with high detection accuracy is provided.

The cesium optical pump detector includes a pumping light generation module configured to generate a near-infrared light, a first optical module configured to receive the near-infrared light and convert the near-infrared light into a circularly polarized light, a magnetic resonance module including a radiofrequency coil configured to generate a radiofrequency electromagnetic field, and an absorption chamber including an elemental cesium, configured to generate a modulated near-infrared signal based upon an interaction of the circularly polarized light, the radiofrequency electromagnetic field, and a magnetic field detected, a photoelectric detection module configured to receive the modulated near-infrared signal and convert the modulated near-infrared signal into an electrical signal, and a signal processing module including an amplifying and filtering unit including a first band-pass filter configured to be activated when to coarsely measure a frequency of the electrical signal, and a second band-pass filter configured to be activated when to finely measure the frequency of the electrical signal, a self-oscillation unit electrically connected to the radiofrequency coil to excite the radiofrequency coil, including a first phase shifter electrically connected to the first band-pass filter, and a second phase shifter electrically connected to the second band-pass filter, a measuring unit electrically connected to the self-oscillation unit, configured to measure the frequency of the electrical signal, and a calculating unit electrically connected to the measuring unit.

In one embodiment, the second band-pass filter includes a plurality of first frequency band selection elements, the second phase shifter includes a plurality of second frequency band selection elements respectively corresponding to the plurality of first frequency band selection elements, and each of the plurality of first frequency band selection elements and each of the plurality of second frequency band selection elements corresponding to each other are configured to define one frequency band for finely measuring the frequency of the electrical signal.

In one embodiment, the amplifying and filtering unit includes a pre-amplifier and a post-amplifier, an input of the post-amplifier being electrically connected to the pre-amplifier, an output of the post-amplifier being respectively and electrically connected to the first band-pass filter and the second band-pass filter.

In one embodiment, the cesium optical pump detector further includes a temperature control module electrically connected to the magnetic resonance module, configured to control a temperature in the absorption chamber.

In one embodiment, the temperature control module includes a fuzzy PID controller.

In one embodiment, the cesium optical pump detector further includes a second optical module disposed between the absorption chamber and the photoelectric detection module, configured to focus the modulated near-infrared signal on the photoelectric detection module.

In one embodiment, the cesium optical pump detector further includes an attitude compensation module fixedly disposed relative to the magnetic resonance module, configured to monitor an angle between the circularly polarized light output from the first optical module and a flux line of the magnetic field detected.

In one embodiment, the photoelectric detection module includes a photodiode configured to receive the modulated near-infrared signal, and a photoelectric conversion circuit electrically connected to the photodiode, configured to convert the modulated near-infrared signal into the electrical signal.

In one embodiment, the cesium optical pump detector further includes a terminal control module respectively and electrically connected to the pumping light generation module, the magnetic resonance module, the photoelectric detection module, and the signal processing module.

In one embodiment, an inner wall of the absorption chamber is coated with paraffin.

In the present disclosure, the frequency of the electrical signal is firstly measured coarsely via the first band-pass filter and the first phase shifter, the frequency bands for working of the second band-pass filter and the second phase shifter are selected according to the coarsely measured frequency of the electrical signal to finely measure the frequency of the electrical signal, so that the ACWs can be found efficiently and accurately.

DETAILED DESCRIPTION

For a clear understanding of the technical features, objects and effects of the present disclosure, specific embodiments of the present disclosure will now be described in detail with reference to the accompanying drawings. It is to be understood that the following description is merely exemplary embodiments of the present disclosure, and is not intended to limit the scope of the present disclosure.

Figure 1:
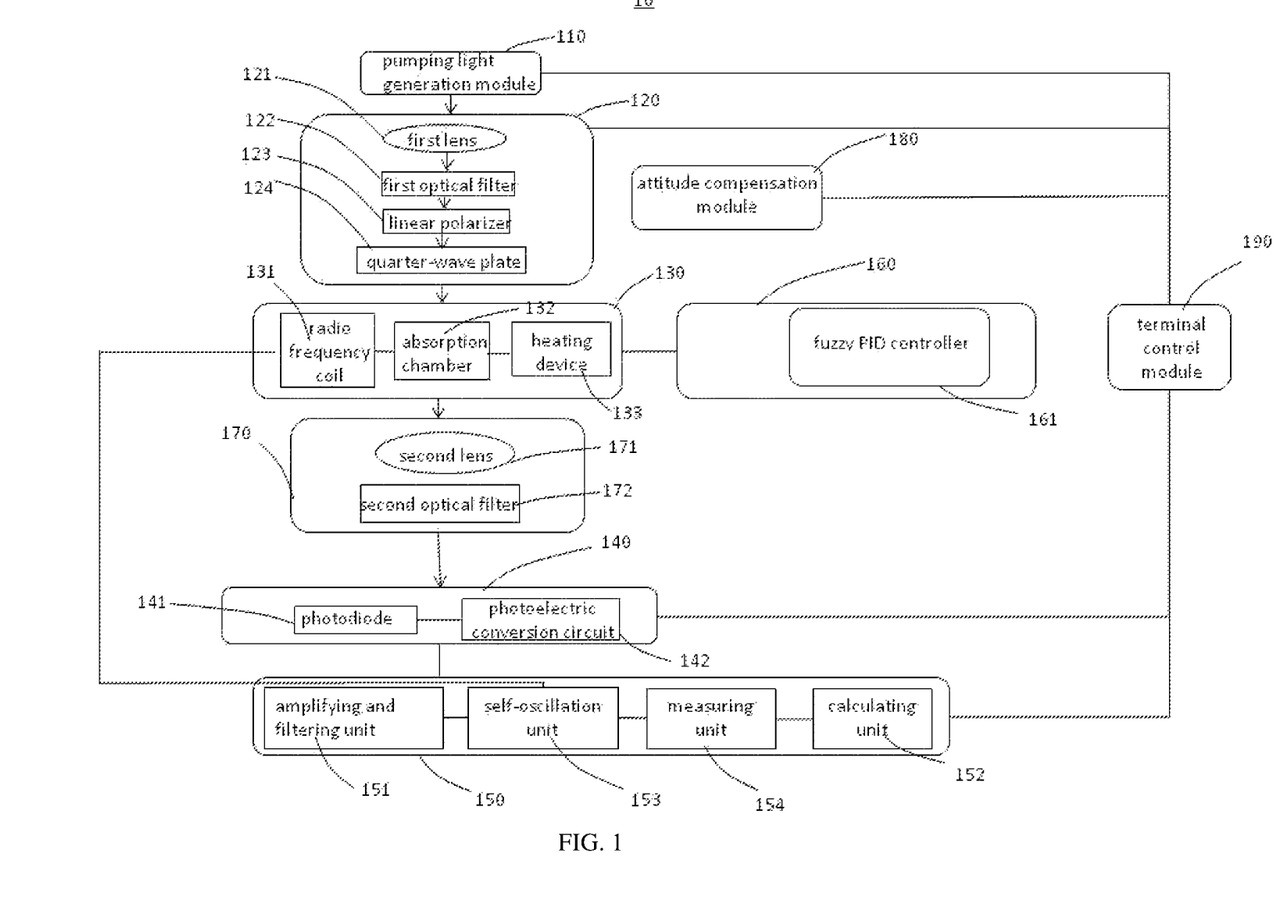
FIG. 1 is a module diagram of one embodiment of a cesium optical pump detector for buried and abandoned chemical weapons.
Figure 2:
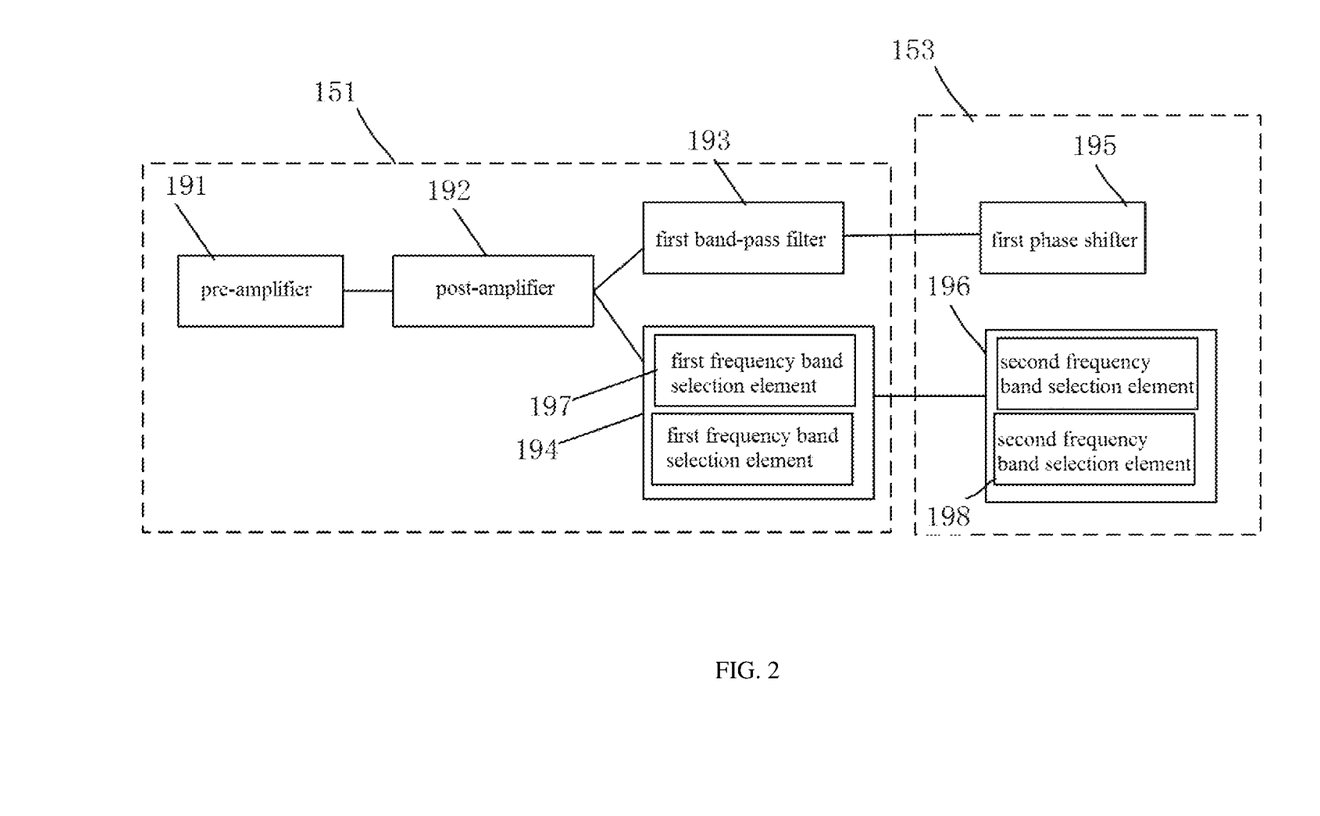
FIG. 2 is a schematic diagram of one embodiment of an amplifying and filtering unit and a self-oscillation unit.

Referring to FIG. 1 and FIG. 2, one embodiment of a cesium optical pump detector 10 for the ACWs includes a pumping light generation module 110, a first optical module 120, and a magnetic resonance module 130. The magnetic resonance module 130 can include an absorption chamber 132 and a radiofrequency coil 131. The pumping light generation module 110 is configured to generate a near-infrared light. The first optical module 120 is configured to receive the near-infrared light and convert the near-infrared light into a circularly polarized light. The absorption chamber 132 can include an element cesium to absorb the circularly polarized light. The radiofrequency coil 131 is configured to generate a radiofrequency electromagnetic field. An opto-magnetic resonance can be occurred to the elemental cesium based upon an interaction of the circularly polarized light, the radiofrequency electromagnetic field, and a magnetic field detected, so as to form a modulated near-infrared signal. More specifically, the circularly polarized light is used to pump electrons from a lower energy level of a cesium atom to a higher energy level. When a frequency of the radiofrequency electromagnetic field is regulated to be substantially equal to a frequency of a transition from the higher energy level to the lower energy level, the opto-magnetic resonance can occur. A resonant frequency of the cesium atom, i.e. a frequency f of the modulated near-infrared signal, is directly proportional to an intensity B of the magnetic field detected according to an equation of $B=(2\pi/\gamma)f$, wherein r is a gyromagnetic ratio of the cesium atom (which is a constant). Therefore, by processing the modulated near-infrared signal, the intensity B of the magnetic field detected can be obtained, and a substance detected can be indentified according to the intensity B.

In one embodiment, the inner wall of the absorption chamber 132 is coated with paraffin to reduce relaxation phenomenon.

In one embodiment, the pumping light generation module 110 can include a semiconductor laser configured to generate the near-infrared light with a wavelength of about about 894 nm.

In one embodiment, the first optical module 120 can include a first lens 121, a first optical filter 122, a linear polarizer 123, and a quarter-wave plate 124. The near-infrared light from the pumping light generation module 110 is configured to pass through the first lens 121, the first optical filter 122, the linear polarizer 123, and the quarter-wave plate 124 in sequence. The first lens 121 is configured to expand a beam of near-infrared lights to parallel lights. The first optical filter 122 configured to filter out stray lights from the parallel lights. The linear polarizer 123 is configured to convert the parallel lights into linearly polarized lights. The quarter-wave plate 124 is configured to convert the linearly polarized lights into the circularly polarized lights and shoot the circularly polarized lights into the absorption chamber 132.

The cesium optical pump detector 10 can further include a photoelectric detection module 140 and a signal processing module 150. The photoelectric detection module 140 is configured to receive the modulated near-infrared signal and convert the modulated near-infrared signal into an electrical signal. In one embodiment, the photoelectric detection module 140 can include a photodiode 141 and a photoelectric conversion circuit 142 electrically connected to the photodiode 141. The photodiode 141 is configured to receive the modulated near-infrared signal and transfer the modulated near-infrared signal to the photoelectric conversion circuit 142. The photoelectric conversion circuit 142 is configured to convert the modulated near-infrared signal into the electrical signal.

The signal processing module 150 can be electrically connected to the photoelectric detection module 140 and configured to receive and process the electrical signal to obtain the intensity B of the magnetic field detected. The signal processing module 150 can include an amplifying and filtering unit 151, a self-oscillation unit 153, a measuring unit 154, and a calculating unit 152 electrically connected in sequence. The amplifying and filtering unit 151 is configured to amplify the electrical signal. The self-oscillation unit 153 is configured to input the electrical signal amplified into the measuring unit 154. The self-oscillation unit 153 can be further electrically connected to the radiofrequency coil 131 for exciting the radiofrequency coil 131. The measuring unit 154 is configured to measure a frequency of the electrical signal. The calculating unit 152 is configured to calculate the intensity B of the magnetic field detected based upon the frequency of the electrical signal.

The amplifying and filtering unit 151 can include a first band-pass filter 193 used to coarsely measure the frequency of the electrical signal and a second band-pass filter 194 used to finely measure the frequency of the electrical signal. The self-oscillation unit 153 can include a first phase shifter 195 and a second phase shifter 196. The first phase shifter 195 can be electrically connected to the first band-pass filter 193. The second phase shifter 196 can be electrically connected to the second band-pass filter 194. When to measure the frequency of the electrical signal, the first band-pass filter 193 and the first phase shifter 195 can be firstly activated to coarsely measure the frequency of the electrical signal. Frequency bands for working of the second band-pass filter 194 and the second phase shifter 196 can be selected according to the coarsely measured frequency of the electrical signal so that the frequency of the electrical signal can be further finely measured, thereby increasing a detection efficiency and a detection accuracy of the cesium optical pump detector 10.

In one embodiment, the second band-pass filter 194 can include a plurality of first frequency band selection elements 197. The second phase shifter 196 can include a plurality of second frequency band selection elements 198 respectively corresponding to the plurality of first frequency band selection elements 197. In one embodiment, the second band-pass filter 194 can be a LC filter. A bandwidth of a frequency band of the second band-pass filter 194 can be in a range from about 70 kz to about 350 kz. The first frequency band selection element 197 and/or the second frequency band selection element 198 can respectively include a high-speed analog switch and a variode connected to the high-speed analog switch. In one embodiment, a plurality of frequency band groups, each of which includes one first frequency band selection element 197 and one second frequency band selection element 198, can be included. Each frequency band group can define one frequency band. The frequency bands for working of the second band-pass filter 194 and the second phase shifter 196 can be selected from the plurality of frequency bands defined by the plurality of frequency band groups according to the coarsely measured frequency of the electrical signal. For example, there can be totally six frequency band groups: 70 kHz-93 kHz, 93 kHZ-121 kHz, 121 kHz-158 kHz, 158 kHz-206 kHz, 206 kHz-269 kHz, and 269 kHz-350 kHz. By narrowing the frequency bands for working of the second band-pass filter 194 and the second phase shifter 196, the frequency of the electrical signal can be further finely measured, thereby increasing a detection efficiency and a detection accuracy of the cesium optical pump detector 10.

In one embodiment, the amplifying and filtering unit 151 can further include a pre-amplifier 191 and a post-amplifier 192. An input of the post-amplifier 192 is electrically connected to the pre-amplifier 191. An output of the post-amplifier 192 is respectively and electrically connected to the first band-pass filter 193 and the second band-pass filter 194. The pre-amplifier 191 can include a Junction Field-Effect Transistor (JEFT) having ultra-low noise. The pre-amplifier 191 can be powered independently with a stable voltage to avoid interferences. Each frequency band group can further include an operational amplifier such as with a high speed and high precision.

The cesium optical pump detector 10 can further include a terminal control module 190 respectively and electrically connected to the pumping light generation module 110, the magnetic resonance module 130, the photoelectric detection module 140, and the signal processing module 150. In one embodiment, the terminal control module 190 can include a STM32 chip. The terminal control module 190 can be configured to control the cesium optical pump detector 10 to generate the near-infrared light. The actuation of the coarse measurement and the fine measurement of the frequency of the electrical signal can be controlled by the terminal control module 190. The frequency of the electrical signal coarsely measured can be transferred to the terminal control module 190. The terminal control module 190 can control the selection of the frequency band used in the fine measurement according to the coarsely measured frequency of the electrical signal. In one embodiment, the terminal control module 190 can be configured to display the intensity of the magnetic field detected and/or the information of the substance detected on a display device.

The cesium optical pump detector 10 can further include a temperature control module 160 electrically connected to the magnetic resonance module 130 to regulate a temperature in the absorption chamber 132. In order to achieve the optical pumping reaction, the elemental cesium should be turned into steam (for example, at a temperature no less than 43° C.). In one embodiment, the temperature in the absorption chamber 132 is regulated to about 50° C. By regulating the temperature in the absorption chamber 132 within a certain range, the detection accuracy can be further improved.

In one embodiment, the magnetic resonance module 130 can further include a heating device 133, such as a heating coil, configured to heat the absorption chamber 132. The temperature in the absorption chamber 132 can be regulated by controlling the heating device 133. The temperature control module 160 can further include a control circuit to control the heating device 133 and a temperature detection circuit to detect an actual temperature in the adsorption chamber 132.

Figure 3:
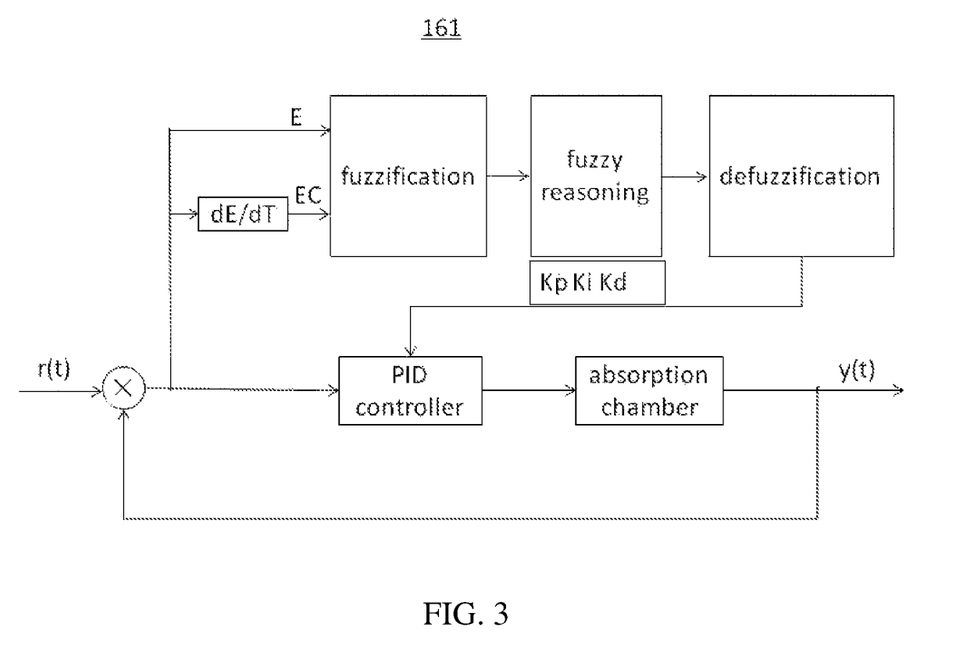
FIG. 3 is a schematic diagram of one embodiment of a fuzzy PID controller.

Referring to FIG. 3, in one embodiment, the temperature control module 160 can further include a fuzzy PID controller 161. The characteristics such as nonlinear, time-varying, and inertial delay can be controlled by using a fuzzy algorithm to eliminate interferences appeared in the detection process. The fuzzy PID controller 161 can realize on-line correction of three parameters: a proportionality coefficient Kp, an integral time constant Ki, and a differential time constant Kd. When the temperature control module 160 is used, a deviation E between the actual temperature in the adsorption chamber 132 and a preset temperature and a deviation variation rate EC can be input into the fuzzy PID controller 161 as input variables and fuzzified. In a process of fuzzification, a fuzzy logic decision is made on the deviation E and the deviation variation rate EC and a fuzzy reasoning algorithm and a defuzzification approach are applied to process information. Finally, three output variables of the fuzzy PID controllers 161, ΔKp, ΔKi, and ΔKd, are output and controlled on-line. The on-line adjustment is made to meet the self-tuning requirements of parameters of the fuzzy PID controller.

The process of fuzzification of the fuzzy PID controller 161 can specifically include: fuzzifying accurate values of the input variables (i.e. the deviation E and the deviation variation rate EC) to acquire linguistic variables. The deviation E and the deviation variation rate EC are quantized to 13 levels, {−6, −5, −4, −3, −2, −1, 0, 1, 2, 3, 4, 5, 6}, by selecting the linguistic variables to be {NB, NM, NS, ZE, PS, PM, PB}. The output variables, ΔKp, ΔKi, and ΔKd, are quantized to 13 levels, {−6, −5, −4, −3, −2, −1, 0, 1, 2, 3, 4, 5, 6}, by selecting the linguistic variables to be {NB, NM, NS, ZE, PS, PM, PB}. Both the input variables and the output variables use a fuzzy membership function of a triangular set.

The fuzzy reasoning process can include: applying fuzzy reasoning to the fuzzified input variables according to fuzzy control rule to acquire fuzzy values of the output variables. In one embodiment, according to operational experience, Kp can be properly increased at a beginning and a middle of a regulating process to raise a response speed and properly decreased at an end of the regulating process to improve a stability of system. Ki can be relatively smaller at the beginning of the regulating process to prevent integral saturation. The integral action should be moderate at the middle of the regulating process to maintain the stability of the system. The integral action should be improved at the end of the regulating process to decrease static deviation. A selection of the Kd value has a great influence on the adjustment of the dynamic characteristics. The differential action should be improved at the beginning of the regulating process to decrease or even avoid overshoot. Kd should be relatively smaller at the middle of the regulating process which is sensitive to Kd. Kd should be further decreased at the end of the regulating process to suppress disturbance. In one embodiment, a table of the fuzzy control rule for parameters of PID is listed as following:

| $\Delta Kp/\Delta Ki/\Delta Kd$ | | NB | NM | NS | EC ZE | PS | PM | PB |
|---|---|---|---|---|---|---|---|---|
| E | NB | PB/NB/PS | PB/NB/NS | PM/NM/NB | PM/NM/NB | PS/NS/NB | ZE/ZE/NB | ZE/ZE/PS |
| | NM | PB/NB/PS | PB/NB/NS | PM/NM/NB | PS/NS/NM | PS/NS/NM | ZE/ZE/NS | NS/NS/ZE |
| | NS | PM/NB/ZE | PM/NM/NS | PM/NS/NM | PS/NS/NM | ZE/ZE/NS | NS/PS/NS | NS/PS/ZE |
| | ZE | PM/NM/ZE | PM/NM/NS | PS/NS/NS | ZE/ZE/NS | NS/PS/NS | NM/PM/NS | NM/PM/ZE |
| | PS | PS/NM/ZE | PS/NS/ZE | ZE/ZE/ZE | NS/PSZE | NS/PS/ZE | NM/PM/ZE | NM/PB/ZE |
| | PM | PS/ZE/PB | ZE/ZE/NS | NS/PS/PS | NM/PM/PS | NM/PM/PS | NM/PB/PS | NB/PB/PB |
| | PB | ZE/ZE/PB | ZE/ZE/PM | NM/PS/PM | NM/PM/PM | NM/PM/PS | NB/PB/PS | NB/PB/PB |

A process of defuzzification, a process, in fuzzy logic, of producing a useful result from fuzzy data, can include defuzzifying the fuzzy values of the output variables by using a weighted average method to acquire accurate values of $\Delta Kp$, $\Delta Ki$, and $\Delta Kd$.

The cesium optical pump detector 10 can further include a second optical module 170 disposed between the absorption chamber 132 and the photoelectric detection module 140, configured to focus the modulated near-infrared signal on the photoelectric detection 140. The second optical module 170 can include a second lens 171 configured to focus the modulated near-infrared signal on the photoelectric detection 140 and a second optical filter 172 configured to reduce noise of the modulated near-infrared signal. In one embodiment, the second optical filter 172 can be a narrow-band pass filter.

The cesium optical pump detector 10 can further include an attitude compensation module 180 fixedly disposed relative to the magnetic resonance module 130. The attitude compensation module 180 is configured to monitor an angle between the circularly polarized lights output from the first optical module 120 and the magnetic field detected. When detecting the magnetic field of the ACWs, the angle between an optical path of the circularly polarized lights and flux lines of the magnetic field detected should be larger than 6° to ensure a normal work of the cesium optical pump detector 10. The attitude compensation module 180 can include a gyroscope, a triaxial accelerometer, and a digital compass. A change of a direction of the circularly polarized lights can be measured by the gyroscope and the accelerometer. A direction of the flux lines of the magnetic field detected can be measured by the digital compass. The gyroscope, the triaxial accelerometer, and the digital compass can be further electrically connected to the terminal control module 190 respectively.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present. The terms "vertical", "horizontal", "left" and "right" and other similar expressions used herein is for the purpose of describing particular embodiments only and is not intended to be limiting of the invention.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. A cesium optical pump detector for buried unexploded ordnance, comprising:
    a pumping light generation module configured to generate a near-infrared light;
    a first optical module configured to convert the near-infrared light into a circularly polarized light;
    a magnetic resonance module comprising:
        a radiofrequency coil configured to generate a radiofrequency electromagnetic field; and
        a cesium absorption chamber comprising an elemental cesium, wherein based upon an interaction of the circularly polarized light, the radiofrequency electromagnetic field, and a magnetic field detected, the elemental cesium is caused to generate an optomagnetic resonance to output a modulated near-infrared signal;
    a photoelectric detection module configured to receive the modulated near-infrared signal and convert the modulated near-infrared signal into an electrical signal; and
    a signal processing module electrically connected to the photoelectric detection module, comprising: an amplifying and filtering unit, a self-oscillation unit, a magnetic resonance frequency measuring unit, and a calculating unit which are sequentially and electrically connected, wherein
        the amplifying and filtering unit comprising:
            a first band-pass filter configured to coarsely measure a frequency of the electrical signal; and
            a second band-pass filter configured to finely measure the frequency of the electrical signal;
        the self-oscillation unit is further electrically connected to the radiofrequency coil to excite the radiofrequency coil, comprising:
            a first phase shifter electrically connected to the first band-pass filter; and
            a second phase shifter electrically connected to the second band-pass filter; and
        the second band-pass filter comprises a plurality of first frequency band selection elements, the second phase shifter comprises a plurality of second frequency band selection elements respectively corresponding to the plurality of first frequency band selection elements, and each of the plurality of first frequency band selection elements and each of the plurality of second frequency band selection elements corresponding to each other are configured to define one frequency band for finely measuring the frequency of the electrical signal.

2. The cesium optical pump detector of claim 1, wherein the amplifying and filtering unit comprises:
    a pre-amplifier; and
    a post-amplifier electrically connected to the pre-amplifier, the post-amplifier is further electrically connected to the first band-pass filter and the second band-pass filter.

3. The cesium optical pump detector of claim 1, further comprising:
a temperature control module electrically connected to the magnetic resonance module, configured to control a temperature in the cesium absorption chamber.

4. The cesium optical pump detector of claim 3, wherein the temperature control module comprise a fuzzy PID controller.

5. The cesium optical pump detector of claim 1, further comprising:
a second optical module disposed between the cesium absorption chamber and the photoelectric detection module, configured to focus the modulated near-infrared signal on the photoelectric detection module.

6. The cesium optical pump detector of claim 1, further comprising:
an attitude compensation module fixedly disposed relative to the magnetic resonance module, configured to monitor an angle between the circularly polarized light output from the first optical module and a flux line of the magnetic field detected.

7. The cesium optical pump detector of claim 1, wherein the photoelectric detection module comprises:
a photodiode configured to receive the modulated near-infrared signal; and
a photoelectric conversion circuit electrically connected to the photodiode, configured to convert the modulated near-infrared signal into the electrical signal.

8. The cesium optical pump detector of claim 1, further comprising:
a terminal control module respectively and electrically connected to the pumping light generation module, the magnetic resonance module, the photoelectric detection module, and the signal processing module.

9. The cesium optical pump detector of claim 1, wherein an inner wall of the cesium absorption chamber is coated with paraffin.

10. The cesium optical pump detector of claim 1, wherein the first optical module comprises:
a first lens configured to expand a beam of the near-infrared light to a parallel light;
a first optical filter configured to filter out a stray light from the parallel light;
a linear polarizer configured to convert the parallel light into a linearly polarized light; and
a quarter-wave plate configured to convert the linearly polarized light into the circularly polarized light and shoot the circularly polarized light into the cesium absorption chamber.

11. A cesium optical pump detector for buried unexploded ordnance, comprising:
a pumping light generation module configured to generate a near-infrared light;
a first optical module configured to convert the near-infrared light into a circularly polarized light;
a magnetic resonance module comprising:
a radiofrequency coil configured to generate a radiofrequency electromagnetic field; and
a cesium absorption chamber comprising an elemental cesium, wherein based upon an interaction of the circularly polarized light, the radiofrequency electromagnetic field, and a magnetic field detected, the elemental cesium is caused to generate an optomagnetic resonance to output a modulated near-infrared signal;
a photoelectric detection module configured to receive the modulated near-infrared signal and convert the modulated near-infrared signal into an electrical signal; and
a signal processing module electrically connected to the photoelectric detection module, comprising: an amplifying and filtering unit, a self-oscillation unit, a magnetic resonance frequency measuring unit, and a calculating unit which are sequentially and electrically connected, wherein
the amplifying and filtering unit comprising:
a first band-pass filter configured to coarsely measure a frequency of the electrical signal; and
a second band-pass filter configured to finely measure the frequency of the electrical signal;
the self-oscillation unit is further electrically connected to the radiofrequency coil to excite the radiofrequency coil, comprising:
a first phase shifter electrically connected to the first band-pass filter; and
a second phase shifter electrically connected to the second band-pass filter;
the second band-pass filter comprises a plurality of first frequency band selection elements, the second phase shifter comprises a plurality of second frequency band selection elements respectively corresponding to the plurality of first frequency band selection elements, each of the plurality of first frequency band selection elements and each of the plurality of second frequency band selection elements corresponding to each other are configured to define one frequency band for finely measuring the frequency of the electrical signal;
and
the calculating unit is configured to calculated an intensity of the magnetic field detected based upon the frequency of the electrical signal;
and
a terminal control module electrically connected to the signal processing module, configured to acquire the frequency of the electrical signal coarsely acquired and select frequency bands for working of the second band-pass filter and the second phase shifter based upon the frequency of the electrical signal coarsely acquired when to finely measure the frequency of the electrical signal.

12. The cesium optical pump detector of claim 11, wherein the amplifying and filtering unit comprises:
a pre-amplifier; and
a post-amplifier electrically connected to the pre-amplifier, the post-amplifier is further electrically connected to the first band-pass filter and the second band-pass filter.

13. The cesium optical pump detector of claim 11, further comprising:
a temperature control module electrically connected to the magnetic resonance module, configured to control a temperature in the cesium absorption chamber.

14. The cesium optical pump detector of claim 13, wherein the temperature control module comprise a fuzzy PID controller.

15. The cesium optical pump detector of claim 11, further comprising:
a second optical module disposed between the cesium absorption chamber and the photoelectric detection module, configured to focus the modulated near-infrared signal on the photoelectric detection module.

16. The cesium optical pump detector of claim 11, further comprising:
   an attitude compensation module fixedly disposed relative to the magnetic resonance module, configured to monitor an angle between the circularly polarized light output from the first optical module and a flux line of the magnetic field detected.

17. The cesium optical pump detector of claim 11, wherein the photoelectric detection module comprises:
   a photodiode configured to receive the modulated near-infrared signal; and
   a photoelectric conversion circuit electrically connected to the photodiode, configured to convert the modulated near-infrared signal into the electrical signal.

18. The cesium optical pump detector of claim 11, wherein the first optical module comprises:
   a first lens configured to expand a beam of the near-infrared light to a parallel light;
   a first optical filter configured to filter out a stray light from the parallel light;
   a linear polarizer configured to convert the parallel light into a linearly polarized light; and
   a quarter-wave plate configured to convert the linearly polarized light into the circularly polarized light and shoot the circularly polarized light into the cesium absorption chamber.

* * * * *